US 9,873,648 B2

(12) United States Patent
Leyshon et al.

(10) Patent No.: US 9,873,648 B2
(45) Date of Patent: Jan. 23, 2018

(54) OXIDATIVE METHODS OF PHOSPHORUS REMOVAL FROM LIQUID HYDROCARBONS

(71) Applicant: Lyondell Chemical Technology, L.P., Houston, TX (US)

(72) Inventors: David W. Leyshon, Houston, TX (US); Lei Zhang, League City, TX (US); Robert Bruce Maskell, Humble, TX (US); Daniel F. White, Houston, TX (US)

(73) Assignee: Lyondell Chemical Technology, L.P., Houston, TX (US)

(*) Notice: Subject to any disclaimer, the term of this patent is extended or adjusted under 35 U.S.C. 154(b) by 0 days.

(21) Appl. No.: 14/920,658

(22) Filed: Oct. 22, 2015

(65) Prior Publication Data

US 2016/0115102 A1 Apr. 28, 2016

Related U.S. Application Data

(60) Provisional application No. 62/068,307, filed on Oct. 24, 2014.

(51) Int. Cl.
*C07C 7/148* (2006.01)
*C07C 7/152* (2006.01)
(Continued)

(52) U.S. Cl.
CPC .......... *C07C 7/14833* (2013.01); *C07C 2/36* (2013.01); *C07C 7/005* (2013.01); *C07C 7/10* (2013.01);
(Continued)

(58) Field of Classification Search
CPC .. C07C 2/18; C07C 6/02; C07C 7/148; C07C 7/152
(Continued)

(56) References Cited

U.S. PATENT DOCUMENTS 2,269,302 A * 1/1942 Atwell ............... C07C 2/62
585/702
3,642,935 A * 2/1972 Dunning et al. ....... B01J 31/143
502/117
(Continued)

FOREIGN PATENT DOCUMENTS

EP 0506314 A2 9/1992
WO WO 01/85654 A2 11/2001

OTHER PUBLICATIONS

International Search Report and Written Opinion dated Jan. 19, 2016 for PCT/US2015/057049.

*Primary Examiner* — Thuan D Dang

(57) ABSTRACT

Provided herein in is a method of removing phosphorus from a liquid hydrocarbon that includes the steps of (a) contacting the liquid hydrocarbon with an aqueous solution that comprises an oxidizing agent to form a reaction mixture that comprises an aqueous component and a hydrocarbon component, wherein the liquid hydrocarbon comprises at least an alkene$_{(C4-30)}$ and a phosphine$_{(C\leq30)}$; (b) reacting the oxidizing agent with the phosphine$_{(C\leq30)}$ to form the corresponding phosphine oxide$_{(C\leq30)}$; and (c) separating the aqueous component from the hydrocarbon component, thereby removing the phosphine oxide$_{(C\leq30)}$ from the liquid hydrocarbon.

14 Claims, 7 Drawing Sheets

(51) Int. Cl.
*C07C 2/18* (2006.01)
*C07C 6/02* (2006.01)
*C07C 2/36* (2006.01)
*C10G 27/04* (2006.01)
*C07C 7/00* (2006.01)
*C07C 7/10* (2006.01)

(52) U.S. Cl.
CPC ...... *C07C 7/14858* (2013.01); *C07C 7/14875* (2013.01); *C10G 27/04* (2013.01)

(58) Field of Classification Search
USPC ....... 585/509, 513, 527, 528, 529, 853, 854, 585/864
See application file for complete search history.

(56) References Cited

U.S. PATENT DOCUMENTS 3,900,304 A * 8/1975 Rehmus .................... C21B 3/08
423/224
6,492,568 B1 12/2002 Murray et al.

* cited by examiner

OXIDATIVE METHODS OF PHOSPHORUS REMOVAL FROM LIQUID HYDROCARBONS

CROSS-REFERENCE TO RELATED APPLICATIONS

This application claims benefit and priority of U.S. Provisional Patent Application No. 62/068,307, filed on Oct. 24, 2014, the content of which is incorporated herein by reference in its entirety.

BACKGROUND OF THE INVENTION

I. Field of the Invention

The present disclosure relates to methods of removing phosphorus compounds from liquid hydrocarbons, including, for example, an oxidative method of removing phosphines from liquid hydrocarbons, such as byproducts from propylene metathesis production processes or olefin conversion technology, including mixtures resulting from the production of butenes.

II. Background

Tighter specifications for hydrocarbon-based fuels is one of the driving forces for the removal of phosphorus impurities from liquid hydrocarbons and fractions that are used to make hydrocarbon fuels, such as kerosene, gasoline, jet fuel, diesel, etc. Hydrocarbon effluent from the propylene metathesis production process or olefin conversion technology, which is a liquid hydrocarbon comprising longer chain hydrocarbon olefins (C≥4), is one of the feedstocks that is blended together with other hydrocarbon fractions to make, for example, gasoline. One source of the hydrocarbon effluent from propylene metathesis production or olefin conversion technology is as a byproduct from the production of butenes (useful for making propylene) from the dimerization of ethylene. When catalysts using phosphorus-based ligands are used in the butenes manufacturing process, the resulting liquid hydrocarbon may contain phosphorus compounds, for example, as free ligands. In some cases, the presence of these phosphorus compounds impurities may make the liquid hydrocarbon less suitable for blending into gasoline. Methods for effectively and efficiently removing such phosphorus compounds from liquid hydrocarbons are therefore desirable.

SUMMARY

In one aspect of the present disclosure, there are provided methods for removing phosphorus compounds from a reaction mixture. In some embodiments, the method of removing phosphorus compounds from a liquid hydrocarbon comprises:

(a) contacting the liquid hydrocarbon with an aqueous solution comprising an oxidizing agent to form a reaction mixture comprising an aqueous component and a hydrocarbon component, wherein the liquid hydrocarbon comprises at least an alkene$_{(C4-30)}$ and a phosphine$_{(C \leq 30)}$;

(b) reacting the oxidizing agent with the phosphine$_{(C \leq 30)}$ to form the corresponding phosphine oxide$_{(C \leq 30)}$;

(c) separating the aqueous component from the hydrocarbon component, thereby removing the phosphine oxide$_{(C \leq 30)}$ from the liquid hydrocarbon.

In some embodiments, the oxidizing agent is sodium hypochlorite (NaClO), potassium hypochlorite, calcium hypochlorite, hydrogen peroxide, chlorine gas, bromine gas, ozone, sodium percarbonate, sodium perborate, chlorine dioxide, oxygen, air, alkyl$_{(C \leq 12)}$ peroxide, aryl$_{(C \leq 12)}$ peroxide, or aralkyl$_{(C \leq 12)}$ peroxide. In some embodiments, the oxidizing agent is NaClO. In other embodiments, the oxidizing agent is t-butyl hydroperoxide (TBHP). In some embodiments, the aqueous solution is neutral. In other embodiments, the aqueous solution is acidic. In other embodiments, the aqueous solution is basic. In some embodiments, the aqueous solution has a pH from 11 to 14. In some embodiments, the aqueous solution has a pH of about 13. In some embodiments, the aqueous solution comprises sodium hydroxide (NaOH), potassium hydroxide, lithium hydroxide, calcium hydroxide, barium hydroxide, strontium hydroxide, or magnesium hydroxide. In some embodiments, the aqueous solution contains NaOH. In some embodiments, the phosphine$_{(C \leq 30)}$ is a trialkylphosphine$_{(C \leq 30)}$ and the corresponding phosphine oxide$_{(C \leq 30)}$ is a trialkylphosphine oxide$_{(C \leq 30)}$. In some embodiments, the phosphine$_{(C \leq 30)}$ is a tributylphosphine and the corresponding phosphine oxide$_{(C \leq 30)}$ is tributylphosphine oxide. In some embodiments, the molar ratio of the oxidizing agent to phosphine$_{(C \leq 30)}$ is from about 0.25:1 to about 5:1. In some embodiments, the molar ratio of oxidizing agent to phosphine$_{(C \leq 30)}$ is about 1:1. In some embodiments, step (b) further comprises agitating the aqueous component with the hydrocarbon component. In some embodiments, step (b) further comprises reacting the oxidizing agent with the phosphine$_{(C \leq 30)}$ at a temperature from about 1° C. to about 150° C. In some embodiments, step (b) further comprises reacting the oxidizing agent with the phosphine$_{(C \leq 30)}$ for a time period from about 1 second to about 120 minutes. In some embodiments, the methods further comprise a washing step, wherein the separated hydrocarbon component of step (c) is washed with a second aqueous solution. In some embodiments, the second aqueous wash involves an extraction column. In some embodiments, the liquid hydrocarbon was obtained from a dimerization reaction of ethylene. In other embodiments, the liquid hydrocarbon is gasoline or a gasoline precursor. In some embodiments, the phosphine$_{(C \leq 30)}$ was obtained from a catalyst used to catalyze the dimerization reaction. In some embodiments, the catalyst is a nickel catalyst with one or more phosphine$_{(C \leq 30)}$ ligands. In some embodiments, the liquid hydrocarbon further comprises an alkane$_{(C \leq 30)}$. In some embodiments, the liquid hydrocarbon further comprises alkenes$_{(C5-10)}$. In some embodiments, the methods result in the removal of more than 50% of the phosphorus compounds from the liquid hydrocarbon as measured by X-ray fluorescence and gas-liquid chromatography. In some embodiments, the methods reduce the amount of phosphorus compounds in the liquid hydrocarbon to less than 25 ppm. In some embodiments, if the oxidizing agent is a hypochlorite then the aqueous solution is basic and the reaction is run for a length of time sufficient to convert the organochloride compounds to the corresponding epoxide.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWING

The following drawings form part of the present specification and are included to further demonstrate certain aspects of the present disclosure. The disclosure may be better understood by reference to one of these drawings in combination with the detailed description of specific embodiments presented herein.

Figure 1A:
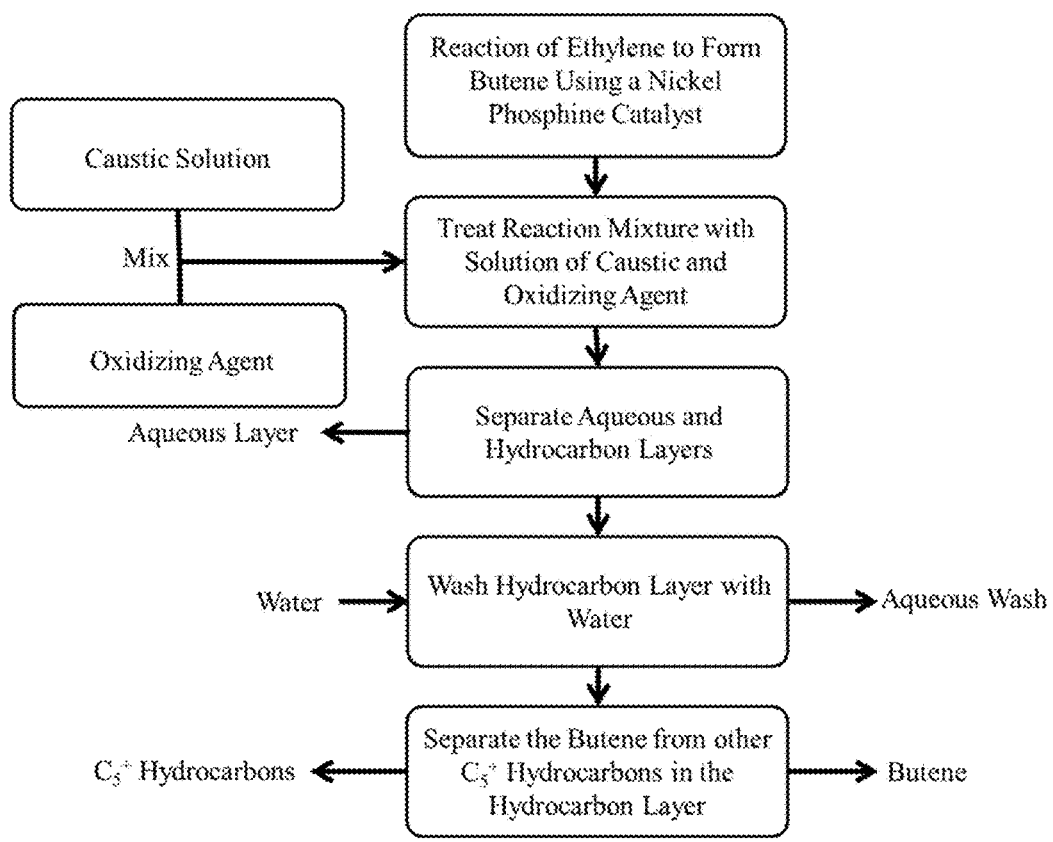
FIG. 1A shows a general overview of an embodiment of a method of removing phosphorus compounds in a butene manufacturing process.

DESCRIPTION OF ILLUSTRATIVE
EMBODIMENTS

The present disclosure provides oxidative methods of removing phosphorus compounds from liquid hydrocarbons. In some aspects, the liquid hydrocarbon is a reaction mixture, e.g., an outflow from a chemical manufacturing process. For example, in some embodiments, the methods comprise treating an outflow from an ethylene dimerization reaction with an oxidizing agent to remove phosphorus compounds from the reaction mixture. In some embodiments, the oxidation agent converts the phosphorus compounds into more water soluble oxidation products (e.g., phosphine oxide compounds), which may then be extracted out of the reaction mixture using water. In some embodiments, the oxidizing agent (e.g., bleach) is added to the reaction mixture in the presence of a caustic agent. In some embodiments, the reaction mixture is washed one or more times with water to remove the oxidation product. In some embodiments, the oxidation of the phosphorus compound causes a >50% reduction of the phosphorus concentration in the treated liquid hydrocarbon.

I. Production of Hydrocarbon Byproducts with
High Levels of Phosphorus Compounds Ethylene dimerization reaction utilizes a catalyst to produce butenes along with higher molecular weight hydrocarbon byproducts and catalyst decomposition products to form a liquid hydrocarbon. This reaction is shown below in Scheme 1.

Scheme 1: General Reaction of Ethylene into Butenes and Other Byproducts

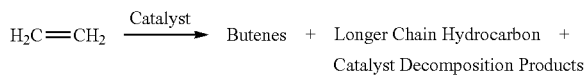

$H_2C$═$CH_2$ $\xrightarrow{\text{Catalyst}}$ Butenes + Longer Chain Hydrocarbon + Catalyst Decomposition Products When the reaction is undergoing this dimerization of ethylene into butene, the amount of catalyst decomposition byproducts remains soluble in the reaction mixture. In some embodiments, the liquid hydrocarbon which comprises the longer chain hydrocarbon byproducts contains high levels of phosphorus compounds after separation. This liquid hydrocarbon is often added to gasoline so long as the total phosphorus compounds content of the gasoline mixture is less than EPA specification of 0.0038 gram per gallon. In order to allow the liquid hydrocarbon to be blended with gasoline in refinery processing, the phosphorus content of the byproduct is ideally below 35 ppm. In some embodiments, when the phosphorus content is higher, the amount of the byproduct which can be added to the gasoline is reduced and has a negative effect on the economic advantages of the process.

II. Removal of Phosphorus Compounds

In some embodiments, there are two particular methods for the removal of the phosphorus compounds from the reaction mixture. In some embodiments, the phosphorus compound is removed from the liquid hydrocarbon through distillation. Using distillation, the liquid hydrocarbon can be separated so that the byproducts are removed from the phosphorus compounds.

In some embodiments, an oxidizing agent can be used to remove the phosphorus compounds from the liquid hydrocarbon. Without being bound by theory, the oxidizing agent causes the phosphine compound to be oxidized to a phosphine oxide and the phosphine oxide is more water soluble than the phosphine compound. In some aspects, all of the byproducts from the oxidation are water soluble and thus are removed from the reaction mixture. In some embodiments, the present disclosure has one or more of the following advantages, the oxidized phosphorus compounds has increased water solubility; the oxidizing agent is relatively stable, compatible with caustic, and is used in stoichiometric or lower amounts to promote a fast oxidizing reaction with the phosphorus compounds, and to generate negligible reaction heat. In some embodiments, the amount of phosphorus in the liquid hydrocarbon is reduced by at least 50%. In some embodiments, the amount is reduced by more than 75%.

III. Process of the Removal of Phosphorus
Compounds from Liquid Hydrocarbon

In some aspects, the present disclosure may relate to a process to remove phosphorus compounds from a liquid hydrocarbon mixture wherein the liquid hydrocarbon mixture is the reaction effluent from butene production. An overview of this process can be found in the drawing.

A. The Production of Butenes in the Presence of a Catalyst

Butene is produced as taught, for example, by U.S. Pat. No. 3,482,001 and U.S. Pat. No. 3,709,953, which are incorporated by herein by reference. In some embodiments, the resulting butene mixtures contain 1-butene and 2-butenes in the form of cis-2-butene and trans-2-butene. The process also produces catalytic decomposition products including nickel salt, aluminum salt, chloride, and phosphorus compounds. In some embodiments, the concentration of the catalytic decomposition products in the reaction byproduct is 1 to 200 ppm nickel, 5 to 2000 ppm aluminum, 10 to 500 ppm chlorine, and 2 to 200 ppm phosphorus.

B. Forming a Mixture of a Caustic Substance and an Oxidizing Agent to Form a Caustic/Oxidizing Mixture.

In some embodiments, in order to remove the phosphorus compounds, a solution comprising a caustic and oxidizing agent is prepared. In some embodiments, the solution comprises a caustic aqueous mixture which contains from about 0.1 wt. % to about 50 wt. % of the caustic. The wt. % of the compounds is based upon the total weight of the aqueous mixture. In some embodiments, the solution contains from about 0.5 wt. % to about 15 wt. % of the caustic. In some embodiments, the solution contains about 8 wt. % of the caustic. In other embodiments, the solution contains about 1 wt. % of the caustic. In some embodiments, the remainder of the solution is water.

In some embodiments, the solution further comprises an oxidizing agent. In some embodiments, the oxidizing agent is added to the solution with the caustic. In other embodiments, the oxidizing agent is prepared in a separate solution. In some embodiments of the present disclosure, the amount of oxidizing agent corresponds to the amount of phosphorus compounds remaining in the system. One aspect of the present disclosure, the amount of oxidizing agent in the wash solution is from about 2 wt. % to about 15 wt. % of the oxidizing solution. In some embodiments, the molar ratio of the oxidizing agent to the phosphorus compound is from about 0.1 to about 25. In some embodiments, the molar ratio is about 0.25 to about 10. In other embodiments, the molar ratio is from about 0.5 to about 10. In some embodiments, the molar ratio is from about 1 to about 2.5.

In some embodiments, the use of bleach or sodium hypochlorite as an oxidizing agent results in the formation of chlorinated hydrocarbons. Without wishing to be bound by any theory, it is believed that one possible chlorination pathway is shown by Equation 1 below. Under basic condition, the chlorohydrin intermediate can further proceed with a bimolecular nucleophilic substitution to form epoxide thereby eliminate chloride in the final gasoline product.

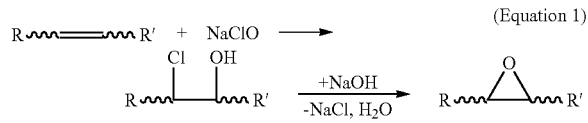

(Equation 1)

Chloride and chlorine compounds can poison the automobile converter just as phosphorus compounds do and chlorinated byproducts may also reduce the disproportion catalyst performance in the olefin production process if these compounds are allowed to remain in the process. Thus, in some embodiments, the liquid hydrocarbon contains less than about 250 wt. ppm of chlorine. In some embodiments, the amount of chlorine is less than 50 wt. ppm. In some embodiments, the amount of chlorine is less than 2 wt. ppm.

Furthermore, in some embodiments of the present disclosure, the order of addition of the caustic to the oxidizing solution is important. The oxidizing agent, in some embodiments, is mixed with the caustic solution and then added to the hydrocarbon reactor effluent. In some embodiments, the oxidizing solution can be added after the injection of caustic solution to the reactor effluent.

In some embodiments, the caustic comprises a basic compound. In some embodiments, the caustic gives the aqueous solution a pH greater than 9. In some embodiments, the basic solution has a pH from about 11 to about 14. In some embodiments, the pH is about 13. In some embodiments, the caustic compound is a metal hydroxide compound which is water soluble. In some embodiments, the caustic substance is sodium hydroxide (NaOH), potassium hydroxide (KOH), calcium hydroxide (Ca(OH)$_2$), barium hydroxide (Ba(OH)$_2$), strontium hydroxide (Sr(OH)$_2$), lithium hydroxide (LiOH), or magnesium hydroxide (Mg(OH)$_2$). In other embodiments, the aqueous solution is neutral. In other embodiments, the aqueous solution is acidic.

In some embodiments, the oxidizing agent is a chemical compound which causes the oxidation of phosphorus compounds to a phosphine oxide compound. In some embodiments, the oxidizing agent is a metal hypochlorite, hydrogen peroxide, alkyl peroxide, aryl or aralkyl peroxide, chlorine gas, bromine gas, metal percarbonate, metal perborate, chlorine dioxide, oxygen, air, and ozone. In some embodiments, the metal in the oxidizing agent is sodium, lithium, magnesium, calcium, or potassium. In some embodiments, the metal is sodium. In other embodiments, the metal is calcium or potassium. In some embodiments, the oxidizing agent is a metal hypochlorite. The oxidizing agent in some embodiments is sodium hypochlorite or potassium hypochlorite. In some embodiments, the oxidizing agent is sodium hypochlorite. In other embodiments, the oxidizing agent is t-butyl hydroperoxide (TBHP), air, or $H_2O_2$.

In some aspects of the present disclosure, the mixture of the caustic and oxidizing agent should not lead to the decomposition of either the caustic or the oxidizing agent. In some embodiments, the oxidizing agent is less volatile than butene or the other hydrocarbon effluent.

C. Adding the Caustic/Oxidizing Mixture from B to the Liquid Hydrocarbon.

Figure 1B:
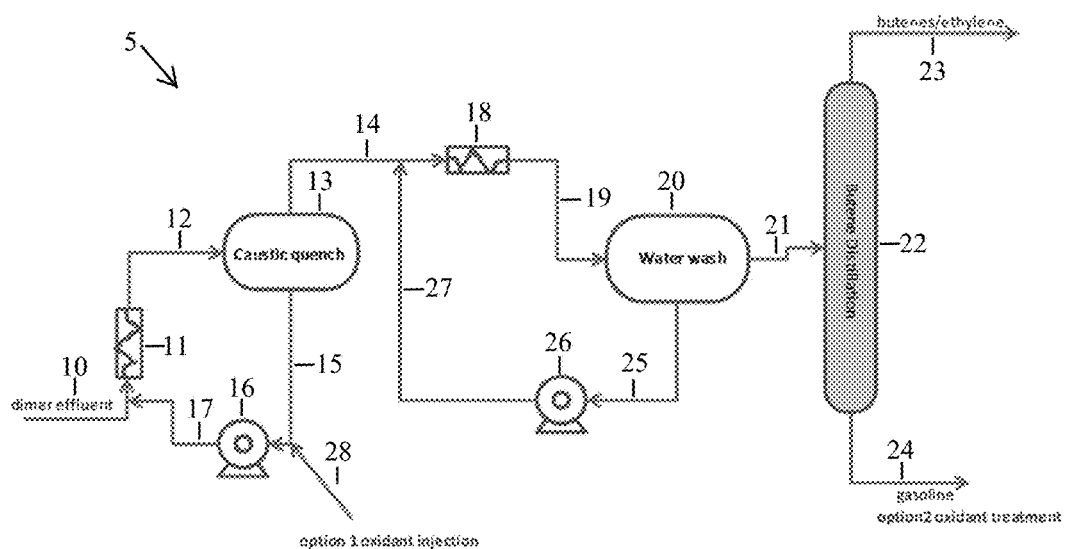
FIG. 1B shows a generalized process setup overview of embodiments of removing phosphorus compounds in a butene manufacturing system.

As shown in FIG. 1B, process flow 5 shows the introduction of the dimer effluent via feed line 10 into the a mixer, in this case a static mixer, 11. Caustic which may also contain an oxidant in Option 1 is introduced via line 17. The caustic is recycled via 15, which is then transferred by pump 16 into line 17. New oxidant is introduced to line 15 via line 28. The mixture is then transferred via line 12 to extraction reactor 13. The hydrocarbon component is transferred via line 14 to a mixer, in this case a static mixer, 18 with water introduced to line 14 via line 27. The mixture is then transferred to washing column 20 via line 19. The hydrocarbon is separated from the water and removed via line 21. The water is removed via line 25 which is then recycled through pump 26 to line 27. The hydrocarbon in line 21 is transferred to distillation column 22. The shorter hydrocarbons, such as ethylene or butene, are removed via line 23 while longer hydrocarbons which may be blended to obtain gasoline are removed via line 24. The longer hydrocarbons may also be treated using the process described in process flow 45.

1. Butene Reactor Effluent (FIG. 1A/FIG. 1B Option 1)

The mixture described in B may be used to remove phosphorus from a butene reactor effluent. In some embodiments of the present disclosure, the caustic solution which contains an oxidizing agent as described in B is added to the butene reactor effluent. In other embodiments, the reactor effluent is added to a solution containing the oxidizing agent after the reactor effluent has been treated with the caustic solution. When the aqueous solution containing the oxidizing agent and the caustic is added to the hydrocarbon effluent, the reaction mixture forms two fractions: an aqueous phase and a hydrocarbon phase. In some aspects, the treating the reactor effluent with the caustic solution comprises adding the caustic solution to the reactor effluent and then removing the aqueous phase. In some embodiments, treating the reactor effluent further comprises mixing the two solutions. In other embodiments, treating the hydrocarbon effluent comprises adding the caustic solution to the reactor effluent without removing the aqueous caustic solution. In some embodiments, the ratio of caustic and oxidizing agent solution to the reactor effluent when measured by weight is from about 2:1 to about 1:8. In some embodiments, the ratio is from about 1:2 to about 1:6. In some embodiments, the ratio is 1:4.

2. Phosphine Removal Gasoline Precursor (FIG. 1B Option 2)

In another aspect, the method comprises treating a gasoline precursor stream with the mixture of the oxidizing agent under conditions sufficient to cause the oxidation of the phosphine to a phosphine oxide. In some embodiments, the gasoline precursor stream results from the mixture of a butene dimerization reaction long chain hydrocarbon byproducts with other $C_5$-$C_8$ hydrocarbons. In some embodiments, the method comprises treating composition after the butene and the ethylene components have been separated from the $C_5$ and greater hydrocarbons. In some embodiments, the addition of the mixture of the aqueous solution containing the oxidizing agent to the gasoline precursor stream allows for a faster reaction due to increased concentration of phosphorus, decreased likelihood of undesirable chlorinated hydrocarbon by-products affecting downstream operation, increased selection of potential oxidizing agent, and increased phosphorus concentration reduction in the final gasoline product. When the gasoline precursor stream is treated with an oxidant mixture, the mixture of the oxidizing agent may further comprise a caustic such as a metal hydroxide. In other embodiments, the mixture does not contain a caustic and the gasoline precursor stream is treated with an oxidizing agent. Furthermore, in some embodiments, the mixture of the oxidizing agent solution and the gasoline is separated such that the aqueous solution containing the oxidized phosphorus compound is separated from the hydrocarbon phase. The hydrocarbon phase may be further processed to obtain gasoline or other refinery products or exposed to additional aqueous washes to increase the amount of phosphine oxide removed from the gasoline precursor. This process is described in process flow 45 of FIG. 2. The gasoline precursor stream is transported via feed line 50 to the hydrocarbon/oxidant mixer 51. As the gasoline precursor is transported, oxidant is introduced into feed line 50 by recycle line 59 along with any recycled oxidant. New oxidant is introduced to recycle line 59 by the oxidant feed 60 through feed line 61 which is transported by pump 62 into feed line 63 which introduces the oxidant into recycle line 59. After mixing the hydrocarbon and oxidant in the mixer 51, the mixture is transported via line 52 to extraction column 53. Water is introduced to the column by feed line 54. Gasoline is separated via output 55. The oxidant and water are removed via output line 56 and fed through pump 57 to waste line 58 which contains spent aqueous.

Figure 6:
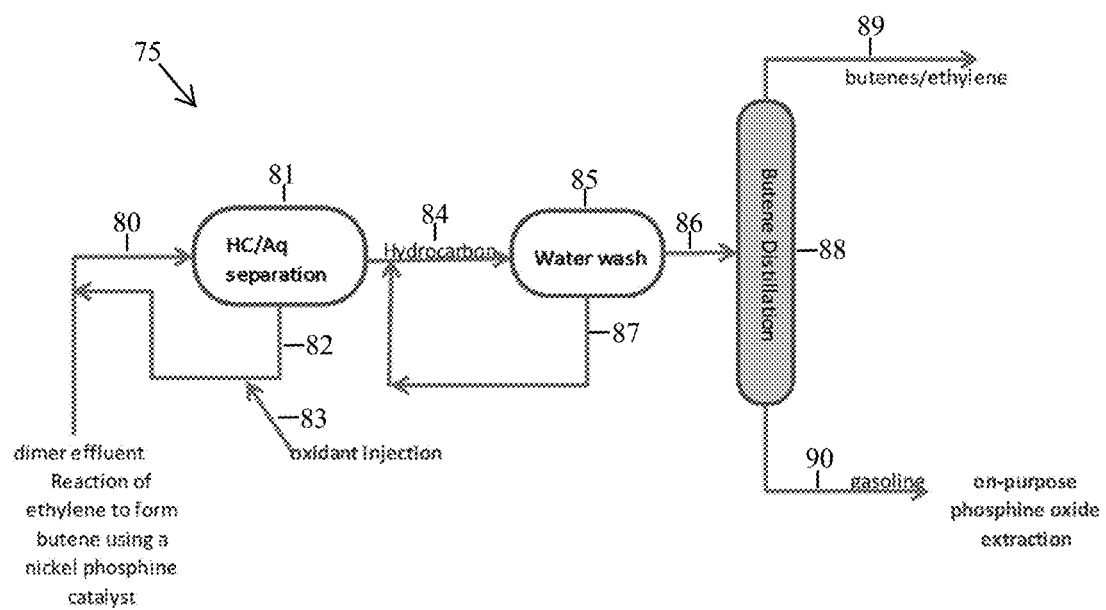
FIG. 6 shows the use of the oxidant is used to treat reactor effluent. After the separation of ethylene and butene from the $C_5$ and higher hydrocarbon byproduct, an on-purpose phosphine oxide extraction column is utilized to further reduced the final gasoline stream phosphorus level.

In another aspect, when the oxidant is added at Option 1 (new oxidant injected via line 28) the process may be combined with the extraction column 53 of process flow 45, such that the butene reactor effluent is treated with the oxidant and then after separation of butene, the gasoline precursor is then subjected to an additional extraction step after the separation of butene from the reaction mixture (FIG. 6). In some embodiments, the additional extraction step comprises using a water wash or extraction column to increase the amount of the phosphine oxide removed from the gasoline precursor. In some embodiments, process flow 75 in FIG. 6 shows that the dimer effluent is transferred via feed line 80 into a hydrocarbon/aqueous extraction reactor 81. The oxidant is added to feed line 80 via the recycle stream 82 which returns the aqueous layer and remaining oxidant to the dimer effluent. New oxidant is added to recycle stream 82 via feed line 83. The hydrocarbon portion after extraction is transported via line 84 to water wash 85. The aqueous component is returned to the hydrocarbon portion via recycle stream 87. The hydrocarbon is separated from the aqueous component and removed via line 86 to butene distillation column 88. The shorter hydrocarbons such as ethylene and butene are separated via output line 89, while longer hydrocarbons that are blended to obtain gasoline are removed via output line 90. The longer hydrocarbons in line 90 may be subjected to a second extraction process such as that shown in process flow 45 of FIG. 2, such as extraction column 53.

3. General Phosphine Oxidation Conditions

In some aspects of the present disclosure, the removal of the phosphine with an oxidizing agent comprises heating the mixture of the caustic solution containing the oxidizing agent to a temperature from about 1° C. to about 70° C. In some embodiments, the temperature is from about 10° C. to about 70° C. In some aspects, the removal of the phosphine comprises pressurizing the reaction mixture to a pressure from about 100 to 300 pounds per square inch (about 690 to about 2100 kPa). In some embodiments, the pressurization is enough to prevent the reaction mixture from vaporizing the reaction components. In some aspects, the reaction comprises reacting for a time period from about 1 second to about 240 minutes. In some embodiments, the reaction time period is from about 1 second to about 120 minutes. In some embodiments, the reaction time period is from 1 second to 60 minutes. In some embodiments, the reaction time period is greater than 30 seconds. Without being bound by theory, the reaction time period is long enough to remove the phosphine compound from the reaction mixture. Furthermore, in some embodiments, the reaction mixture further comprises subjecting the aqueous solution containing the caustic agent and the oxidizing agent with the liquid hydrocarbon solution to mixing through mechanical mixing.

In some embodiments, the caustic solution leads to the removal of some of the catalytic decomposition product including but not limited to the aluminum, nickel, and chloride compounds from the decomposition of the catalyst. In some embodiments, the caustic solution does not lead to the removal of the phosphorus compounds in the reactor effluent. In some embodiments, the caustic solution causes the aluminum, nickel, and chloride compounds to solubilize in the aqueous phase. As such, the removal of these compounds reduces the aluminum, nickel, or chloride compounds in the reactor effluent. Addition of the oxidizing agent to the caustic solution converts the phosphorus compound to a phosphine oxide. In some embodiments, the phosphine oxide is soluble in water and is partitioned into the aqueous phase. In some embodiments, the phosphine oxide is partitioned into the aqueous phase with the decomposed aluminum, nickel, and chloride compounds.

In some aspects of the present disclosure, the reaction of the caustic and the oxidizing agent with the liquid hydrocarbon is reacted at a temperature from about 10° C. to about 70° C. In some embodiments, the pressure of the reaction is from about 100 pounds per square inch to about 500 pounds per square inch or about 690 to about 3500 kPa. In some embodiments, the pressure is about 150 pounds per square inch to about 250 pounds per square inch or about 1000 to about 1750 kPa. Some aspects of the present disclosure comprise carrying out the reaction in a set of static mixers.

Without wishing to being bound by theory, the ratio of the amount of oxidizing agent and the phosphorus compound added in the solution is useful to remove the phosphorus compounds from the hydrocarbon solution and minimize the unwanted side reaction such as chlorination by hypochlorite type oxidants. In some embodiments, the ratio of the oxidizing agent to the phosphorus compound is from about 0.1 to about 5. In some embodiments, the ratio is from about 0.2 to about 2.5. In some embodiments, the ratio is from about 0.5 to about 1. Without wishing to be bound by any theory, it is believed that if a molar ratio of greater than 10 equivalents of oxidizing agents compared to the phosphorus compounds represents a concentration which can lead to undesirable byproducts. In some embodiments, when the oxidizing agent is a metal hypochlorite, then the byproducts are organic chloride compounds.

D. Separation of the Aqueous Phase from the Hydrocarbon Phase Containing the Liquid Hydrocarbon.

In some embodiments, after the aqueous phase containing the oxidizing agents is added to the liquid hydrocarbon, the bulk of the aqueous phase is then physically separated from the hydrocarbon phase. In some embodiments, the aqueous phase is removed from the mixture via decanting. Without being bound by theory, the physical separation of the aqueous phase from the hydrocarbon phase through decanting is improved with increased and cleaner separation of the two phases. In some embodiments, the physical separation is achieved at a temperature from about 1° C. to about 100° C., or from about 10° C. to about 70° C. In some embodiments, the pressure of the separation is from about 100 pounds per square inch to about 500 pounds per square inch or about 690 to about 3500 kPa. In some embodiments, the pressure is about 150 pounds per square inch to about 250 pounds per square inch or about 1000 to about 1750 kPa. In some embodiments, the pressure is about 170 pounds per square inch to about 190 pounds per square inch or about 1100 to about 1300 kPa. In some embodiments, the hydrocarbon phase has a lower density than the aqueous phase and thus the hydrocarbon phase separates above the aqueous phase in the reactor.

E. Washing the Hydrocarbon Phase with Water in at Least One Washing Step.

As used herein, "washing" includes extraction by using water. In one embodiment, the washing includes extracting the phosphine oxide out of the hydrocarbon phase using water. After the aqueous solution with the oxidizing agent is removed from the hydrocarbon phase, the hydrocarbon phase can be further washed with water. In some embodiments, the hydrocarbon phase is washed with water 1, 2, 3, 4, 5, or 6 times. In some embodiments, the hydrocarbon phase is washed with water 2, 3, or 4 times. In some embodiments, the hydrocarbon phase is washed with water once. In some embodiments, the hydrocarbon phase is washed with water three times. In some aspects, the wash comprises adding from a volume of water equal to about 20% of the volume of the hydrocarbon phase to about 100% of the volume of the hydrocarbon phase. In some embodiments, the wash volume is greater than 25% of the volume of the hydrocarbon phase. Furthermore, the washing step may further comprise heating the reaction to a temperature from about 1° C. to about 100° C. In some embodiments, the temperature may be from about 10° C. to about 100° C. When water is added to wash the hydrocarbon phase, the reaction mixture comprises two phases: a hydrocarbon phase and an aqueous phase. In some embodiments, the washing step results in the removal of additional catalyst decomposition products, including phosphine oxide. In other embodiments, the washing step may further comprise using an extraction column may be used to further the extraction of the phosphine oxide from the hydrocarbon phase. Extraction columns may include structured packing, or may be a plate column, agitated column, or spray column.

F. The Longer Chain Hydrocarbon Material Present in the Liquid Hydrocarbon is Separated from the Butene.

In some aspects, when the liquid hydrocarbon is a butene reactor effluent, then after the hydrocarbon phase is washed, the longer chain hydrocarbon material (e.g., hydrocarbons containing more than five carbons) is separated from the butene. In some embodiments, the reactor effluent in the hydrocarbon phase comprise from about 75 wt. % to about 99 wt. % butene. In some embodiments, the reactor effluent contains about 85 wt. % to about 98 wt. % butene. In some embodiments, the reactor effluent in the hydrocarbon phase further comprises about 1 wt. % to about 25 wt. % longer chain hydrocarbon byproducts. In some embodiments, the reactor effluent comprises about 2 wt. % to about 15 wt. % longer chain hydrocarbon byproducts. In some embodiments, the reactor effluent comprises about 10 wt. % of the longer chain hydrocarbon byproducts.

In some embodiments, the longer chain hydrocarbon material can be separated from the reactor effluent mixture through distillation. In some embodiments, the longer chain hydrocarbon byproduct is separated via a 30 tray distillation tower.

G. The Purified Butene is Used to Produce Propylene.

After removal of the catalyst decomposition byproducts and the longer chain hydrocarbon solutions when the liquid hydrocarbon is a butene reactor effluent, in some embodiments, the butene can be further processed. In some embodiments, the butene is primarily 2-butene. In other embodiments, the butene is primarily 1-butene. In some embodiments, the butene is used to produce propylene. In other embodiments, the butene is used in other process to produce another material. In other embodiments, the butene is used in the production of a polyolefin such as polyethylene or polypropylene as a co-monomer. Furthermore, in other embodiments, the butene is used to form octenes for detergents through dimerization.

H. Formulation of Liquid Hydrocarbon into Gasoline

In another aspect, the liquid hydrocarbon which has been treated with the aqueous solution containing the oxidizing agent is a gasoline precursor which may be further processed to obtain a commercially useful gasoline. The $C_5$ and greater hydrocarbons may be admixed with one or more other sources of gasoline quality hydrocarbons to obtain a gasoline product which is acceptable for commercial sale. In some embodiments, the gasoline precursor is subjected to further alkylation reactions to increase the alkyl length of the material before formulation into gasoline.

IV. PROCESS SCALE-UP

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated by reference herein.

V. DEFINITIONS

When used in the context of a chemical group: "hydrogen" means —H; "hydroxy" means —OH; "halo" means independently —F, —Cl, —Br or —I;

In the context of chemical formulas, the symbol "—" means a single bond, "=" means a double bond. The symbol "⌇" means a single bond where the geometry around a substitution is undefined. The bond orders described above are not limiting when one of the atoms connected by the bond is a metal atom (M). For the groups and classes below, the number of carbon atoms in the group is as indicated as follows: "Cn" defines the exact number (n) of carbon atoms in the group/class. "C≤n" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. Compare "phosphine$_{(C≤10)}$", which designates phosphine groups having from 0 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. Typically the carbon number indicator follows the group it modifies, is enclosed with parentheses, and is written entirely in subscript; however, the indicator may also precede the group, or be written without parentheses, without signifying any change in meaning Thus, the terms "C5 olefin", "C5-olefin", "olefinz$_{(C5)}$", and "olefin$_{C5}$" are all synonymous.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkane" is a group of the formula: R—H, wherein R is an alkyl group.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkane" is a group of the formula: R—H, wherein R is a cycloalkyl group.

The term "alkenyl" when used without the "substituted" modifier refers to an monovalent unsaturated aliphatic group with a carbon atom as the point of attachment, a linear or branched acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkene" is a group of the formula: R—H, wherein R is an alkenyl group.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The terms "phosphine" and "phosphane" are used synonymously herein. When used without the "substituted" modifier these terms refer to a compound of the formula PR$_3$, wherein each R is independently hydrogen, alkyl, cycloalkyl, alkenyl, aryl, or aralkyl, as those terms are defined above. Non-limiting examples include PMe$_3$, PBu$_3$, PtBu$_3$, PPh$_3$, and PCy$_3$ (tricyclohexylphosphine). The terms "trialkylphosphine" and "trialkylphosphane" are also synonymous. Such groups are a subset of phosphine, wherein each R is an alkyl group.

The term "phosphine oxide" when used without the "substituted" modifier refers to a compound of the formula O=PR$_3$, wherein each R is independently hydrogen, alkyl, cycloalkyl, alkenyl, aryl, or aralkyl, as those terms are defined above. Non-limiting examples include OPMe$_3$ (trimethylphosphine oxide), OPBu$_3$ (tributylphosphine oxide), and PPh$_3$O (triphenylphosphine oxide).

The term "phosphorus compounds" are used to refer to compounds containing one or more phosphorus atoms with the molecular formula. The term "phosphorus" when used in the context of a composition refers to a composition containing one or more phosphorus compounds as that term is defined above or elemental phosphorus. Alternatively, this term may also be used to reference to the concentration of phosphorus atoms in the composition.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "gasoline" is used to describe a $C_5$ or greater hydrocarbon containing composition which has been prepared for use as a fuel source in an internal combustion engine. The term "gasoline precursor" refers to a composition which contains $C_5$ or greater hydrocarbons that is added to other hydrocarbon material to obtain gasoline.

The term "hydrocarbon" is used to refer to a composition of organic compounds contain one or more carbon atoms and comprises at least 90% molecules with only carbon and hydrogen. The term "liquid hydrocarbon" and "hydrocarbon by-product" are used interchangeably to refer to a composition containing multiple different aliphatic, aromatic, or both compounds from a composition arising from the production of butene or other higher carbon length products such as gasoline. The term "hydrocarbon effluent" or "reactor effluent" is a subset of liquid hydrocarbon wherein the liquid hydrocarbon is from the production of an ethylene dimerization process to produce butene and contains $C_5$ or longer hydrocarbons.

An "isomer" of a first compound is a separate compound in which each molecule contains the same constituent atoms as the first compound, but where the configuration of those atoms in three dimensions differs.

A "method" is series of one or more steps undertaking lead to a final product, result or outcome. As used herein, the word "method" is used interchangeably with the word "process".

An "oxidizing agent" is a compound or composition capable of causing an increase in the oxidation state of another compound. In some aspects, the oxidizing agent is a compound which can transform a phosphine into a phosphine oxide. Some non-limiting examples of oxidizing agents include metal chlorite, peroxide compounds, and air or other sources of molecular oxygen.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present disclosure.

VI. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

A. Experimental

Materials: Samples of hydrocarbon effluent from the propylene metathesis production process were collected from plant. De-ionized (DI) water was used directly. A commercially available bleach solution containing 8.25 wt. % NaClO was purchased. 50 wt. % NaOH aqueous solution, heptane and n-octene were ordered from Fisher and used as received. A 200 g NaClO stock solution ($1.0 \times 10^{-5}$ mol/g) was prepared with 1.8 g bleach ($2.0 \times 10^{-3}$ mol NaClO, 1.6 mL) and 198.2 g DI water. An 8 wt. % caustic was prepared from 16 g 50 wt. % NaOH aqueous solution and 84 g DI water. $H_2O_2$ (30 wt. % in water) solution and t-butyl hydrogen peroxide (TBHP, 70 wt. % in water) were used as purchased.

Characterization: The total phosphorus and chloride were analyzed by an x-ray fluorescence (XRF) method with a detection limit for P of 5 ppm and Cl of 10 ppm. Specific phosphorus species (trialkylphosphine and trialkylphosphine oxide) were quantified by GC-FID. The organic chloride was analyzed by GC-AED with a detection limit of 0.5 ppm.

Samples S1 and S2: 100 mL plant sample (66 g, 53 µmol tributylphosphine, plant sample ID# FG1) was placed inside a 500 mL round bottom flask, followed by 0.50 g bleach (8.25 wt. %, 554 µmol NaClO). The mixture was stirred and heated at 800 RPM and 60° C. for 1 h (under reflux). The hydrocarbon layer was collected and a fraction of it was submitted for testing as sample S1. Another 60 mL of the above treated hydrocarbon effluent was subjected to a 60 mL DI water wash under room temperature (RT). The washed hydrocarbon effluent was submitted for testing as sample S2.

Samples S3: The procedure for the S2 was repeated except that 1) the plant sample was a different batch (100 mL, 13 µmol tributylphosphine, plant sample ID# FG2); 2) 100 mL DI water was added together with 0.50 g bleach; 3) no intermediate sampling after the bleach reaction; and 4) 100 mL DI water was used to wash 100 mL treated hydrocarbon effluent solution to get the final sample.

Samples S4 and S5: A 1:1 molar ratio of NaClO to tributylphosphine was used. 31.4 g of a plant sample ($3.2 \times 10^{-5}$ mol tributylphosphine), plant sample ID# FG3, 179.0 g heptane, 52.5 g 8 wt. % caustic and 3.2 g dilute bleach ($1.0 \times 10^{-5}$ mol/g, $3.2 \times 10^{-5}$ mol NaClO) were added to a flask under $N_2$. The mixture was heated at 60° C. for 30 min with 700 RPM stirring. After separation from the aqueous phase (55.23 g), the organic phase was washed with 52.5 g DI water. 207.79 g organic phase was collected after separating 52.57 g aqueous phase. The hydrocarbon phase was distilled to remove 85 wt. % of the sample overhead. The bottom 15 wt. % residual (34.20 g) was labeled as sample S5 while the last cut of the distillate (30.45 g) collected at 96.2-96.98° C. was label as S4. Both samples were submitted for total P, Cl and phosphorus species testing.

Sample S6: A 1:1 molar ratio of NaClO to tributylphosphine was used. 29.0 g of a plant sample ($2.9 \times 10^{-5}$ mol of tributylphosphine, plant sample ID# FG3), 2.9 g dilute bleach ($1.0 \times 10^{-5}$ mol/g, $2.9 \times 10^{-5}$ mol NaClO) were added to a flask under $N_2$. The mixture was heated at 60° C. for 1 hr with 600 RPM stirring. After separation from the aqueous phase (7.15 g), the organic phase was washed with 7.5 g DI water. 26.3 g organic phase was collected after separating 7.45 g aqueous phase. The hydrocarbon phase was label as S6 and submitted for total P, Cl and phosphorus species testing.

Samples S7 and S8: The procedure from samples S7 and S8 were similar to samples S4 and S5 except with 34.67 g of the plant sample ID# FG4 ($2.9 \times 10^{-5}$ mol tributylphosphine), 178 g heptane, 52.5 g 8 wt. % caustic and 2.9 g dilute bleach ($1.0 \times 10^{-5}$ mol/g, $2.9 \times 10^{-5}$ mol NaClO). S7 is the last cut of distillate and S8 is the 15 wt. % residual. Samples were submitted for total P, Cl and phosphorus species testing.

Samples S9: The procedure from sample S9 was similar to sample S5 except with 31.5 g of a plant sample ID# FG5 ($2.9 \times 10^{-5}$ mol tributylphosphine), 178 g octene-1, 52.5 g 8 wt. % caustic and 7.33 g dilute bleach ($1.0 \times 10^{-5}$ mol/g, $7.33 \times 10^{-5}$ mol NaClO). The mixing lasted only 1 min upon bleach injection. And the subsequent DI water wash was performed at 60° C. The 15 wt. % residual was labeled as S9 and submitted for total P, Cl and phosphorus species testing.

Samples S10: The procedure from sample S10 was similar to sample S9 except that 7.25 g dilute bleach ($1.0 \times 10^{-5}$ mol/g, $7.25 \times 10^{-5}$ mol NaClO) was used and the mixing time was 10 sec upon bleach injection. The 15 wt. % residual was labeled as S10 and submitted for total P, Cl and phosphorus species testing.

B. Treatment of Hydrocarbon Effluent with NaClO

Plant hydrocarbon effluent was sampled for a one month period and analyzed by XRF and GC-AED. Due to the susceptibility of tributylphosphine to oxidation (neat tributylphosphine is pyrophoric), sampling containers were switched to Hoke® cylinders from Dopak® bottles for later collections. Still some degree of oxidation by air to tributylphosphine oxide was observed during handling (Table 1). Repeated XRF were conducted with samples collected on different days and the results were reproducible.

TABLE 1

Phosphorus Content of Plant Samples

| Plant sample ID# | XRF | P (wtppm) (From Phosphine and Phosphine Oxide) GC (15.3%, 14.2%) | Phosphine (wtppm) GC | Phosphine Oxide (wtppm) GC |
|---|---|---|---|---|
| FG1 | 51, 54 | 41 (25.0, 15.6) | 163 | 110 |
| FG2 | 64 | 41 (6.1, 35.2) | 40 | 248 |
| FG3 | 53, 55 | 47 (31.4, 15.7) | 205 | 111 |
| FG4 | 60, 61 | 44 (26.0, 18.2) | 170 | 128 |
| FG6 | 70 | 49 (32.7, 16.0) | 214 | 112 |
| FG7 | 65 | 48 (30.0, 18.4) | 196 | 130 |
| FG5 | 73 | 48 (28.8, 19.9) | 188 | 133 |
| FG5 | 66 | 49 (28.5, 20.3) | 186 | 143 |

Trialkylphosphine with excess of NaClO.

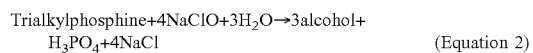
(Equation 2)

Excess NaClO (11~43 equiv) was used initially but only tributylphosphine oxide was observed (Table 2) instead of phosphoric acid ($H_3PO_4$) as suggested by Armour following Eq. 2. Sample S1 was collected after treating plant sample ID# FG1 with 11 equiv. NaClO while sample S2 was obtained after a further equal volume deionized (DI) water washing of sample S1. The results indicated a complete conversion of tributylphosphine to tributylphosphine oxide under process temperature (60° C., Equation 3) and the further washing step was effective at extracting tributylphosphine oxide into aqueous phase to achieve ca. 75% P reduction (to 13 ppm) based on XRF and GC. The phosphorus reduction by bleach was again reproduced with plant sample ID# FG2 as seen with samples S3 vs. FG2.

TABLE 2

Plant Sample Treatment with Excess of Bleach.

| Sample # | Cl (wtppm) XRF | Cl (wtppm) GC | P (wtppm) XRF | P (wtppm) GC | Phosphine (wtppm) GC | Phosphine Oxide (wtppm) GC |
|---|---|---|---|---|---|---|
| FG1 | <10 | — | 51, 54 | 41 (25.0, 15.6) | 163 | 110 |
| S1 | 152 | — | 46 | 38 (0, 38.5) | ND | 271 |
| S2 | 132 | — | 13 | 13 | ND | 90 |
| FG2 | <10 | 1.5 | 64 | 41 (6.1, 35.2) | 40 | 248 |
| S3 | 219 | 69 | 15 | 13 | ND | 94 |

"ND" indicates analyzed but not detected.
"—" not tested.

Treating trialkylphosphine with NaClO.

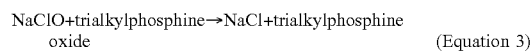
(Equation 3)

Plant sample ID# FG2 was collected in Dopak® bottles. Despite care during the handling, significant oxidation already occurred with tributylphosphine causing NaClO to be greater excess (42 equiv.) when the usage was planned with plant sample ID# FG1 tributylphosphine content. Thus along with good P reduction, appreciable amounts of hydrocarbon chlorination were detected by XRF (from 132 to 219 ppm) and GC.

The reactor byproduct stoichiometric bleach treatment involved diluting a reactor byproduct sample with either heptane or 1-octene to a 15 wt. % reactor byproduct solution, then reacting with 8 wt. % caustic containing bleach in a weight ratio of hydrocarbon effluent: caustic of 4:1, followed by one DI water wash at a hydrocarbon effluent to DI water weight ratio of 4:1. As indicated by gas chromatography, the procedure does not results in significant chlorination of the reactor byproduct under the reaction conditions for samples S4-S5 when the reactor byproduct is diluted with an alkane. The hydrocarbon effluent was then further separated by distillation that bottom 15 wt. % residual and optionally the last fraction of the 85% overhead distillate were analyzed by GC and XRF for phosphorus content and chlorination. The less dilution of the plant sample (15 wt. % vs. 7 wt. % respectively) and the less amount of DI water for washing (4:1 vs. 2:1 respectively) actually diminished the effectiveness of phosphorus reduction by bleach. However, over 80% phosphorus reduction was still achieved (Table 3).

TABLE 3

Plant Sample Treatment with Stoichiometric Bleach Treatment.

| Sample # | Cl (wt. ppm) GC | P (wt. ppm) XRF | P (wt. ppm) GC (15.3%, 14.2%) | Phosphine (wt. ppm) GC | Phosphine Oxide (wt. ppm) GC |
|---|---|---|---|---|---|
| FG3 | — | 53, 55 | 47 (31.4, 15.7) | 205 | 111 |
| S5 | ND | 6 | 6 (4.1, 2.3) | 27 | 16 |
| S6 | 9.7 | 27 | 22 (4.7, 17.1) | 31 | 120 |
| FG4 | 0.9 | 60, 61 | 44 (26.0, 18.2) | 170 | 128 |
| S8 | ND | 16 | 13 (6.1, 6.8) | 40 | 48 |
| FG5 | — | 73 | 48 (28.8, 19.9) | 188 | 133 |
| S9 | 0.7 | 6.8 | 7 (0, 6.8) | ND | 48 |
| S10 | — | <5 | 1 (0, 0.9) | ND | 6 |

ND—analyzed but not detected.
— not tested.

Sample S5 was the bottom 15 wt. % residual from plant sample FG3 treatment using 1:1 molar ratio of NaClO:

tributylphosphine and heptane dilution. Effective P reduction was seen from 50 to 6 ppm by both XRF and GC. The last cut of the distillate (labeled as sample S4) from the same experiment did not show any P and chlorination by XRF and GC. However, treating the plant sample by replacing the caustic with DI water with no hydrocarbon dilution was less effective than S5. P reduction of 50% from 50 to 27 ppm was seen for sample S6. Additionally minor chlorination (9.7 ppm) was identified by GC. The results from samples S5, S4, and S6 have indicated treating a plant sample with 1:1 molar ratio of NaClO to tributylphosphine is capable of reducing P to at least 50% original. Based upon these experiments, dilution of the composition with a hydrocarbon diluent and using the caustic aqueous phase led to increased P reduction and the minimization of chlorination by-products. The P reduction was reproduced with FG4 for sample S8.

The experiments were performed to mimic process conditions with short mixing times and slower agitation rates. Sample S9 was obtained using 1-octene dilution and higher NaClO dosing (a molar ratio of [NaClO]:[tributylphosphine]= 2.5) with the intention to maximize the side chlorination if there was any by increasing the concentration of reactive olefinic moieties and NaClO. The analyses again showed good phosphorus reduction to single digit ppm with negligible chlorination from both XRF and GC-AED. The results were able to be reproduced with sample S10, confirming the effectiveness of NaClO for P reduction at stoichiometric amount with minimal chlorination.

C. Concentration Effects of Oxidizing Agent on the Purification of a Gasoline Precursor Stream Containing Phosphine Table 4A (Conditions) and Table 4B (Results): Experiments with 4000 wt. ppm sodium hypochlorite concentration in 1 wt. % caustic at various reaction times with gasoline precursor samples.

Figure 3:
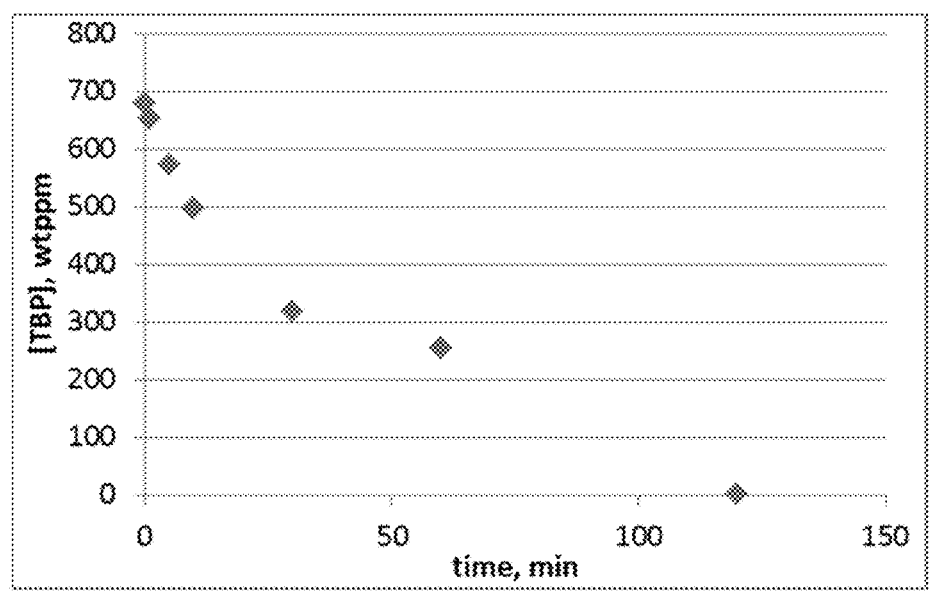
FIG. 3 shows the tributylphosphine concentration in the hydrocarbon phase after various reaction time using 4000 wt. ppm sodium chlorite concentration in 1 wt. % caustic. While maintaining the usage of bleach solution (4000 wt. ppm in 1 wt. % caustic), it was found the reaction is first order on tributylphosphine concentration and the apparent rate constant (k) is rather small, 0.018 $min^{-1}$.

While maintaining the usage of bleach solution (4000 wt. ppm in 1 wt. % caustic), it was found the reaction is first order on [TBP] and the apparent rate constant (k) is rather small, 0.018 min$^{-1}$ (Table 4 and FIG. 3), compared to the reaction of $PH_3$ and NaClO (Lawless et. al., 1962).

Additionally, a canonical analysis was conducted with the process variables and outputs (Table 5). The general trend suggested that the reaction time was useful to reducing the concentration of the phosphine such as TBP, while caustic was useful to reduce chlorine concentration. Both 1 wt. % and 8 wt. % caustic showed similar amounts of chlorinated by-products.

TABLE 5

| Standardized Coefficients for Reaction Variables and Process Output. | | |
|---|---|---|
| [NaClO] | 0.01319 | −0.109361 |
| NaClO:P | −0.380336 | −0.2492 |
| Reaction Temperature | 0.0376579 | 0.0238478 |
| Reaction Time | −0.421028 | −0.841277 |
| Caustic | 0.937527 | −0.276469 |
| TBP | 0.637266 | 1.06911 |
| Cl by GC | −0.47957 | 1.14853 |

Even with the longer reaction time of Experiment 6 of Tables 4A & 4B and an initial chlorine concentration increase, the final gasoline after 120 min bleach treatment had 2 wt. ppm chlorine concentration.

The bleach treated gasoline product (Table 6) has been tested and shown to have comparable quality as the untreated gasoline in corrosion (ASTM D130 and D7571), chlorine concentration content (ASTM D7359), and gumming tendency.

| Run Number | [NaClO] wt. ppm | NaClO:P Molar ratio | NaClO:P Ratio | Reaction Temp. °F. | Reaction Time Min | Gasoline Precursor g | NaClO solution g |
|---|---|---|---|---|---|---|---|
| Starting Material | 0 | 0 | 0 | 0 | 0 | 0 | 0 |
| 1 | 4000 | 3.0 | 2.6 | 68 | 60 | 67.14 | 11.06 |
| 2 | 4000 | 3.0 | 2.5 | 68 | 30 | 67.82 | 10.69 |
| 3 | 4000 | 3.0 | 2.5 | 68 | 10 | 67.49 | 10.72 |
| 4 | 4000 | 3.0 | 2.5 | 68 | 5 | 67.68 | 10.56 |
| 5 | 4000 | 3.0 | 2.5 | 68 | 1 | 67.61 | 10.63 |
| 6 | 4000 | 3.0 | 5.0 | 68 | 120 | 67.58 | 14.63 |

| Run Number | TBP wt. ppm | TBPO wt. ppm | Total P wt. ppm | P (TBP) wt. ppm | Unreacted P wt. % | Cl by GC wt. ppm | P (XRF) wt. ppm |
|---|---|---|---|---|---|---|---|
| Starting Material | 679 | 147 | 125 | 104 | 100.0% | 1.1 | 117 |
| 1 | 255 | 453 | 103 | 39 | 37.6% | 4.0 | 92 |
| 2 | 319 | 376 | 102 | 49 | 47.0% | 3.5 | 104 |
| 3 | 497 | 239 | 110 | 76 | 73.2% | 2.5 | 112 |
| 4 | 572 | 178 | 113 | 88 | 84.2% | 1.8 | 98 |
| 5 | 652 | 148 | 121 | 100 | 96.0% | 1.4 | 118 |
| 6 | 0 | 635 | 90 | 0 | 0.0% | 2.2 | 108 |

TABLE 6

Bleach Treated Gasoline for Quality Comparison.

| Reaction Number | Name | TBP wt. ppm | TBPO wt. ppm | P (Total) wt. ppm | P (TBP) wt. ppm | Unreacted P (%) | Cl wt. ppm |
|---|---|---|---|---|---|---|---|
| 21 | Starting Material | 766 | 137 | 137 | 117 | 100% | 1.1 |
| 22 | 4000 wt. ppm bleach | 113 | 679 | 114 | 17 | 15% | 2 |

Figure 4:
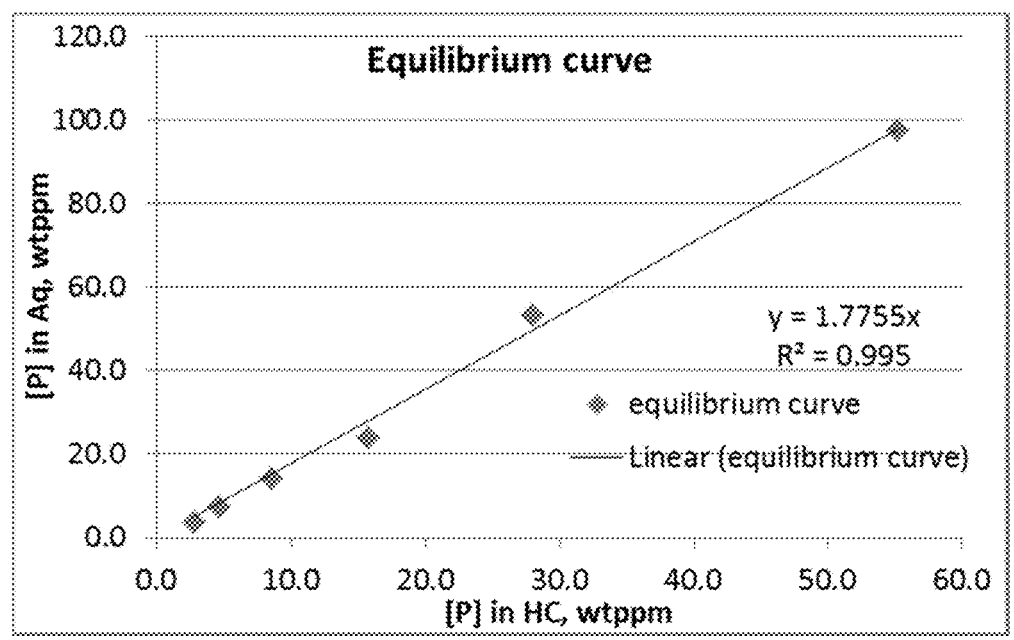
FIG. 4 shows the extraction of tributylphosphine oxide from a gasoline precursor to an aqueous phase at room temperature wherein the gasoline precursor has a phosphorus compound concentration from about 5 to about 100 wt. ppm. The results have shown that the partition coefficient is rather constant at room temperature (about 68° F. to 70° F.) for the proposed phosphorus compound levels from about 5 wt. ppm to about 100 wt. ppm.
Figure 5:
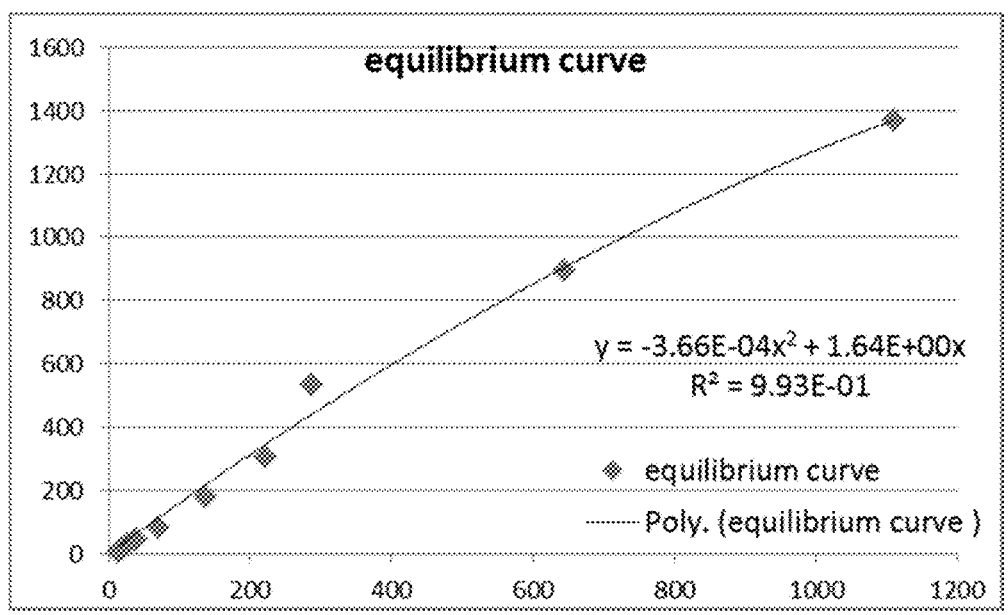
FIG. 5 shows the extraction of tributylphosphine oxide from a gasoline precursor to aqueous at room temperature (phosphorus concentration from about 100 to about 1200 wt. ppm). At higher concentrations of phosphorus, the extraction efficiency was slightly reduced.

Since the aqueous bleach solution used for TBP oxidation was not enough to extract the majority of the formed TBPO, additional extraction were used to reduce the phosphorus concentration in the gasoline product. The results showed that the partition coefficient is rather constant at room temperature (about 68° F. to 70° F.) for the proposed phosphorus levels from about 5 wt. ppm to about 100 wt. ppm (FIG. 4). At higher concentrations of phosphorus (phosphorus concentration of greater than 100 wt. ppm), the extraction efficiency was slightly reduced (FIG. 5).

The partition coefficient is affected by the extraction temperature. Lower temperatures were found to improve TBPO extraction into aqueous phase at ambient pressure (Table 7).

TABLE 7

$K_{pc}$ as a Function of Extraction Temperature under Ambient Pressure.

| T (° C.) | $K_{pc}$ |
|---|---|
| 10 | 2.4 |
| 20 | 1.7 |
| 27 | 0.8 |
| 35 | 0.4 |

Further experiments were conducted with a 3" inner diameter and 20' height glass column and stainless steel structured packing Severe gassing of lighter component was observed at warmer temperature (about 35° C.) and ambient pressure which led to poor TBPO extraction initially. Upon chilling the feeds to 10° C. at ambient pressure, the experiment successfully reduced phosphorus concentration in the gasoline feed from about 80 wt. ppm to about 8 wt. ppm or less by dispersing the hydrocarbon effluent in an aqueous continuous phase. For all of these experiments, the ratio of aqueous phase to the hydrocarbon phase by weight was at least approximately 0.6.

In these experiments, the sodium hypochlorite was able to effectively oxidize tributylphosphine to tributylphosphine oxide. The reaction proceeded with first order reaction kinetics respective of the concentration of tributylphosphine.

The use of caustic allowed for the reaction to proceed with a low concentration of chlorine on the final product.

D. Analysis of Oxygen and Peroxide Based Oxidants

Other oxidants which may also be used to oxidize TBP to TBPO include air, $H_2O_2$, and tert-butyl hydro peroxide (TBHP). The results of oxidations with these oxidizing agents are shown in Table 8. As described in the Table, air and $H_2O_2$ were not as effective as oxidants compared to sodium hypochlorite.

The experiments shown in Table 8 showed that TBHP was effective under these conditions condition to oxidize TBP.

Table 8A (Conditions) and Table 8B (Results): TBP Oxidation with Various Oxidants.

| Reaction Number | Oxidant | Oxidant:P Molar ratio | Reaction Temperature ° F. | Reaction Time min | Gasoline Precursor mL | Water/Oxidant mL |
|---|---|---|---|---|---|---|
| 28 | 30 wt. % $H_2O_2$ | 3 | 68 | 5 | 100 | 6.4 |
| 29 | 30 wt. % $H_2O_2$ | 1 | 68 | 5 | 100 | 2.1 |
| 33 | air | | 68 | 5 | 24 | 48 |
| 34 | air | | 68 | 5 | 24 | 120 |
| 35 | air | | 68 | 5 | 24 | 216 |
| Starting Material | | | | | | |
| 39 | TBHP 70 wt. % in water | 2 | 68 | 5 | 686.15 g | 0.5 |

| Reaction Number | TBP (GC) wt. ppm | TBPO (GC) wt. ppm | Total P (GC) wt. ppm | P by XRF wt. ppm |
|---|---|---|---|---|
| 28 | 708 | 107 | 124 | 110 |
| 29 | 678 | 109 | 119 | 99 |
| 33 | 1117 | 23 | 174 | 140 |
| 34 | 1037 | 16 | 161 | 120 |
| 35 | 1060 | 14 | 164 | 140 |
| Starting Material | 628 | 72 | 106 | 90 |
| 39 | 0 | 650 | 92 | 95 |

Figure 2:
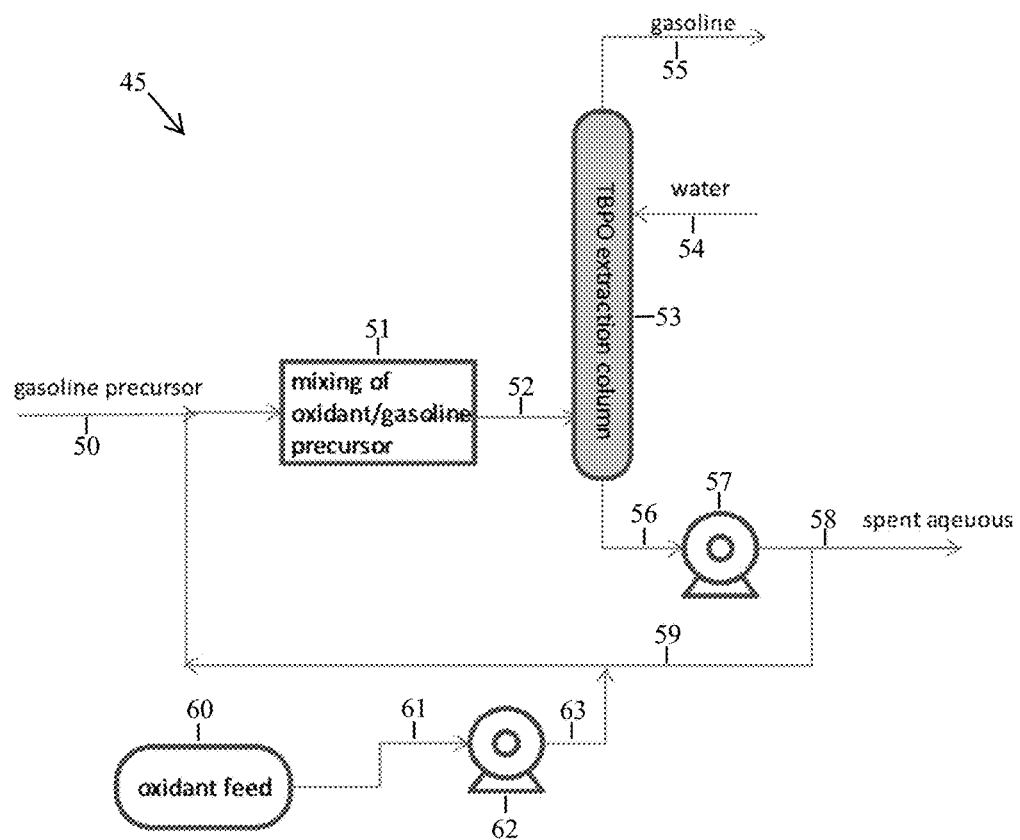
FIG. 2 shows the process flow of an embodiment of a treatment to reduce phosphorus concentration in a gasoline precursor.

Similar to the gasoline treated with sodium hypochlorite, the gasoline treated with TBHP showed no change in corrosion and gumming properties relative to untreated gasoline. A process for treatment of the gasoline precursor stream containing phosphine is shown in FIGS. 2 and 6.

All of the compounds, complexes, and methods disclosed and claimed herein can be made and executed without undue experimentation in light of the present disclosure. While the compounds, complexes, and methods of this disclosure have been described in terms of preferred embodiments, it will be apparent to those of skill in the art that variations may be applied to the compounds, complexes, and methods, as well as in the steps or in the sequence of steps of the method described herein without departing from the concept, spirit, and scope of the disclosure. More specifically, it will be apparent that certain agents which are chemically related may be substituted for the agents described herein while the same or similar results would be achieved. all such similar substitutes and modifications apparent to those skilled in the art are deemed to be within the spirit, scope and concept of the disclosure as defined by the appended claims.

REFERENCES

The following references to the extent that they provide exemplary procedural or other details supplementary to those set forth herein, are specifically incorporated herein by reference.

U.S. Pat. No. 3,482,001
U.S. Pat. No. 3,709,953
Anderson, N. G., *Practical Process Research & Development—A Guide For Organic Chemists*, $2^{nd}$ ed., Academic Press, New York, 2012.
*Hazardous Laboratory Chemicals Disposal Guide*, $3^{rd}$ edition, by Margaret-Ann Armour, Lewis publishers
Klawonn, et. al., "A Simple and Convenient Method for Epoxidation of Olefins without Metal Catalysts," *Adv. Synth. Catal.*, 345(3):389-392, 2003.
Lawless et. al., "812. Kinetics of the reaction between phosphine and sodium hypochlorite in alkaline solution," *J. Chem. Soc.*, 4200-4205, 1962.

What is claimed is:

1. A method comprising:
   (a) contacting a liquid hydrocarbon with an aqueous solution comprising an oxidizing agent to form a reaction mixture comprising an aqueous component and a hydrocarbon component, wherein the liquid hydrocarbon comprises at least an alkene$_{(C4-30)}$, and a phosphine selected from the group consisting of trimethylphosphine, tributylphosphine and triphenylphosphine at a ratio of phosphine to oxidizing agent of 0.25:1-5:1;
   (b) reacting the oxidizing agent with a phosphine selected from the group consisting of trimethylphosphine, tributylphosphine and triphenylphosphine for 10-120 minutes to form a phosphine oxide selected from the group consisting of trimethylphosphine oxide, tributylphosphine oxide and triphenylphosphine oxide; and
   (c) removing the aqueous component comprising phosphine oxide$_{(C\leq30)}$ from the hydrocarbon component; wherein the method reduces the amount of phosphorus in the liquid hydrocarbon to less than 25 ppm.

2. The method of claim 1, wherein the oxidizing agent is selected from the group consisting of sodium hypochlorite (NaClO), potassium hypochlorite, calcium hypochlorite, hydrogen peroxide, chlorine gas, bromine gas, ozone, air, sodium percarbonate, sodium perborate, chlorine dioxide, oxygen, t-butyl hydroperoxide, alkyl$_{(C\leq12)}$ peroxide, aryl$_{(C\leq12)}$ peroxide and aralkyl$_{(C\leq12)}$.

3. The method of claim 1, wherein the aqueous solution is neutral.

4. The method of claim 1, wherein the aqueous solution has a pH greater than 9.

5. The method of claim 1, wherein the aqueous solution comprises sodium hydroxide (NaOH), potassium hydroxide, lithium hydroxide, calcium hydroxide, barium hydroxide, strontium hydroxide, or magnesium hydroxide.

6. The method of claim 1, wherein step (b) further comprises agitating the aqueous component with the hydrocarbon component.

7. The method of claim 1, wherein step (b) further comprises reacting the oxidizing agent with the phosphine at a temperature from about 1° C. to about 150° C.

8. The method of claim 1, further comprising a washing step, wherein the separated hydrocarbon component of step (c) is washed with a second aqueous solution.

9. The method of claim 8, wherein the wash with a second aqueous solution occurs in an extraction column.

10. The method of claim 1, wherein the liquid hydrocarbon was obtained from a dimerization reaction of ethylene.

11. The method of claim 1, wherein the liquid hydrocarbon is gasoline or a gasoline precursor.

12. The method of claim 10, wherein the phosphine was obtained from a catalyst used to catalyze the dimerization reaction.

13. The method of claim 12, wherein the liquid hydrocarbon further comprises an alkane$_{(C\leq30)}$.

14. The method of claim 1, wherein the liquid hydrocarbon further comprises alkenes$_{(C5-10)}$.

* * * * *

UNITED STATES PATENT AND TRADEMARK OFFICE
CERTIFICATE OF CORRECTION

PATENT NO. : 9,873,648 B2  
APPLICATION NO. : 14/920658  
DATED : January 23, 2018  
INVENTOR(S) : Leyshon et al.

Page 1 of 1

It is certified that error appears in the above-identified patent and that said Letters Patent is hereby corrected as shown below:

On the Title Page

Column 2, item (57), under 'Abstract', Line 1, after "herein" delete "in".

In the Specification

In Column 10, Line 28, delete "comprise", and insert -- comprises --.
In Column 11, Line 64, delete "an", and insert -- a --.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*